United States Patent [19]

Singhal

[11] Patent Number: 4,711,839

[45] Date of Patent: Dec. 8, 1987

[54] IMMUNE COMPLEX ASSAY

[75] Inventor: Anil K. Singhal, Edmonds, Wash.

[73] Assignee: IMRE Corporation, Seattle, Wash.

[21] Appl. No.: 690,556

[22] Filed: Jan. 11, 1985

[51] Int. Cl.$^4$ .................. G01N 33/53; G01N 33/564; G01N 33/543; C12Q 1/00

[52] U.S. Cl. ........................................... 435/4; 435/7; 435/68; 435/803; 436/506; 436/507; 436/518; 436/161; 436/821; 436/828

[58] Field of Search ............... 436/507, 506, 518, 524, 436/528, 541, 548, 64, 161, 824, 821, 828; 435/803, 7, 68, 240, 241, 4; 260/112 B, 112 R

[56] References Cited

PUBLICATIONS

Chemical Abstracts, vol. 101, No. 168659Z; 1984.
Kohler and Milstein, Nature, vol. 256, pp. 495–497, 1975.
Jones et al., Journal of Immunological Methods, vol. 44, pp. 249–270, 1981.
Jones, et al., (1980) Cancer 46:675–684.
Hudson and Hay, Practical Immunology, 2nd. edition, Blackwell Scientific Publication, Oxford (1980), pp. 229–230.
HSU, et al., (1981) Am. J. Clin. Pathol., 75:734.
Koprowski et al., (1979) Somatic Cell Genetics 5:957–972.
Dippold et al. (1980) Proc. Natl. Acad. Sci. USA 77:6114–6118.
Gupta et al., (1983) Clin. exp. Immunol. 53:589–599.
Theofilopoulous et al., (1978) J. Clin. Invest. 59:1570–1581.

*Primary Examiner*—Sidney Marantz
*Assistant Examiner*—Patricia L. DeSantis
*Attorney, Agent, or Firm*—Townsend & Townsend

[57] ABSTRACT

A novel method for detecting tumor associated antigen in patient's serum or plasma samples is provided. Tumor associated antigen in the form of immune complexes is detected by first applying the patient's serum sample to an immunoadsorbent column to enrich the amount of immune complexes relative to other serum components. The amount of tumor associated antigen is then detected in the enriched sample in a solid-phase assay employing a solid-phase receptor for the immune complexes and a labelling system specific for the tumor associated antigen.

11 Claims, No Drawings

IMMUNE COMPLEX ASSAY

BACKGROUND OF THE INVENTION

1. Field of the Invention

Over the past decade, there have been numerous reports relating to the identification of tumor associated antigens, also referred to as tumor markers. Such tumor associated antigens may be intracellular or cell surface molecules, typically proteins, glycoproteins, glycolipids, and the like, which are associated with neoplastic cells but not with corresponding normal cells or are associated with normal cells in very small quantities. In some instances, the tumor associated antigens are released from the neoplastic cells into the blood or body fluids, and many attempts have been made to correlate the serum level of such antigens with the presence and/or status of the disease.

Unfortunately, such correlations have been very difficult to make. Ideally, a useful tumor marker would be present in all patients suffering from the tumor, but would be absent from the sera of all normal patients and patients suffering from other types of neoplasia. At present, no such tumor markers have been identified. Instead, it has been found frequently that markers which are identified with the neoplastic transformation of one type of cell will be present on cells of other normal tissues. Conversely, it is also found that markers associated with particular types of tumors in a number of individual patients will not be universally associated with that type of tumor on all patients. Thus, serum assays for virtually all known tumor markers are subject to false positives stemming from release of "tumor" markers from normal cells and false negatives resulting from the lack of universal tumor markers.

For these reasons, it would be desirable to provide improved tumor marker assays capable of furnishing a superior correlation between the presence of the tumor marker and the disease state of the patient. It would be particularly desirable to provide such assays which may be employed with both known and presently undiscovered tumor markers.

2. Description of the Prior Art

Gupta et al. (1983) Clin. Exp. Immunol. 53:589-599 describes the detection of tumor associated antigen in eluates from *Staphylococcus aureus* columns used for the immunoadsorption of plasma from a melanoma patient. Theofilopoulous et al. (1978) J. Clin. Invest. 59:1570-1581 describe an assay for immune complexes employing Raji cells for binding of the immune complexes.

SUMMARY OF THE INVENTION

The present invention provides an improved method for detecting tumor associated antigen in patient plasma or sera. It has been found that an improved correlation between the presence of the tumor associated antigen and the status of the disease is obtained by detecting only that antigen which is present in the form of circulating immune complexes. The assay may be employed with most known tumor markers, and is useful both for screening patient sera to detect the presence of cancer, as well as monitoring the tumor load in patients known to suffer from particular forms of cancer.

Immune complexes between tumor antigen and antibody to the tumor antigen may form freely in plasma. Normally, the presence of antigen in circulation is sufficiently low, or the antigen is present for a sufficiently brief time, that the immune complexes are removed by the phagocytic mechanisms of the immune system. Because of the relatively high concentration of tumor associated antigens in many patients, however, antigen-antibody complexes (known as circulating immune complexes or immune complexes) may persist for long periods of time. It is believed that the formation of these complexes may have two effects which relate to the detection of tumor associated antigen in plasma or sera. First, because the antigen is involved in such complexes, the antigen may be refractory to detection by normal immunoassays. This situation would lead to false negative results as have been observed in the prior art. Second, because low levels of the antigen which may be released by normal cells will usually not form persistent immune complexes, the free antigen may be detected, which leads to false positive results. Both these sources of error may be obviated by detecting tumor associated antigen only as present in immune complexes, as accomplished by the method of the present invention.

The assay of the present invention comprises three essential steps. First, the immune complexes within the patient's serum or plasma sample are enriched relative to other serum components, typically by immunoadsorption. After the initial enrichment, the immune complexes are separated from the enriched fraction, typically by immobilization on a solid-phase receptor specific for the immune complexes. It has been found that the enrichment step followed by the separation of the immune complexes is critical in detecting specific immune complexes which are present at very low levels, typically on the order of less than 1 $\mu$g/ml in serum. After separation, the immune complexes may be detected by conventional immunological techniques, conveniently employing labelled receptors specific for the tumor marker.

DESCRIPTION OF THE SPECIFIC EMBODIMENTS

The present invention provides a novel assay method for detecting the presence of tumor markers in serum or plasma. The method comprises an enrichment step where the serum or plasma sample is passed through an immunoadsorbent column to enrich the concentration of immune complexes present in the sample relative to other serum components in the sample. The immune complexes will be enriched by a factor of at least about 1.2, preferably at least about 2, more preferably at least from about 5 to 10. Following the enrichment step, the immune complexes are separated employing a solid-phase receptor specific for the complexes. Once bound to the solid-phase receptor, the complexes are detected using a labelling system specific for the tumor marker of interest. The amount of tumor marker detected in the sample may then be related to the disease status, typically by reference to a standard curve or by comparison to the patient's individual history.

The enrichment step will utilize an immunoadsorbent column capable of specifically binding immune complexes from the plasma or serum sample. The immunoadsorbent column will employ receptors specific for the immune complexes, such as protein A, antibody to human immunoglobulin, C1q protein, C3b protein, and the like. In some cases, it will be possible to use antibody specific for the tumor marker of interest as the receptor, although this would not be advisable where substantial amounts of free tumor associated antigen are likely to be present in the serum sample. Having the desired receptor, immunoadsorbent columns may be prepared conventionally by coupling the receptor to a suitable column packing, such as Sephadex ®, Sepharose ®, particulate silica, agarose, or the like. A suitable protein A column may be obtained from IMRÉ Corporation, Seattle, Wash., under the trade name Prosorba. Alternatively, packed *Staphylococcus aureus* columns may be prepared and utilized for the enrichment step. The preparation of such *S. aureus* columns is described in detail in Jones et al. (1980) Cancer 46:675-684, the relevant portions of which are incorporated herein by reference.

The method of the present invention also employs a solid-phase receptor for separating the enriched immune complexes obtained from the immunoadsorbent column. Conveniently, the solid-phase will be a test receptacle, such as a test tube or microtiter well, suitable for performing the remainder of the assay. The solid-phase may be constructed from conventional materials, such as glass, polypropylene, polystyrene, and the like. Suitable receptors include Raji cells, as well as the receptors which were described above for use in the immunoadsorbent column. Particularly preferred are the Raji cells and the Clq protein which have very high affinity for the immune complexes.

The receptor will be immobilized in the test receptacles by known techniques. For example, Raji cells may be non-specifically bound to the walls of the test receptacle as follows. Live Raji cells are centrifuged and washed to remove culture fluid. The washed cells are then incubated in the test receptacle for one hour at a low temperature. Clq protein may also be non-specifically adsorbed by incubation for several days at low temperature. Following the non-specific adsorption, the remaining non-specific binding sites should be blocked by incubation with a blocking reagent, such as a gelatin solution or bovine serum albumin. A specific method for binding Clq to polystyrene tubes is described in Hudson and Hay, Practical Immunology, 2nd. edition, Blackwell Scientific Publications, Oxford (1980), pp. 229-230.

The method of the present invention employs a labelling system capable of detecting the tumor associated antigen of interest. The labelling system, in turn, will utilize a receptor specific for the tumor associated antigen, typically an antibody or monoclonal antibody, and a label capable of being detected when immobilized on the solid-phase. Most simply, the labelling system may comprise labelled antibody capable of binding the tumor associated antigen directly. Alternatively, the labelling system may employ an unlabelled primary antibody capable of binding the tumor associated antigen and a labelled secondary antibody capable of binding the primary antibody. Other suitable labelling systems are also available, such as the biotin-avidin bridge labelling technique described by Hsu et al. (1981) Am. J. Clin. Pathol. 75:734.

A wide variety of detectable labels are suitable for use in the present invention. Enzymes are of particular interest, including hydrolases, particularly esterases and glycosidases, and oxidoreductases, particularly peroxidases. Also suitable are radioactive labels, such as $^{125}I$, $^{32}P$, $^{14}C$, and the like; fluorescent compounds such as fluorescine and its derivatives, rhodamine and its derivatives, dansyl, umbelliferone, and the like; and chemiluminescers such as luciferin and luminol, and the like. These detection labels may be used in solid or liquid phase systems.

The assay of the present invention is suitable for detecting virtually any serum tumor marker for which a receptor protein, usually an antibody, can be found or prepared. It is not necessary that the particular tumor marker be a perfect predictor or indicator of the diseased state. In some cases, the presence of amount of the tumor marker in sera may be diagnostic of a neoplastic condition, while in many other cases only variations in the amount of tumor marker present will have substantial significance, usually corresponding to increases and decreases in the tumor load.

Tumor markers of interest include proteins, glycoproteins, glycolipids, and the like. Of particular interest are glycolipids which appear to contain an aberrant ceramide composition which may result from the neoplastic transformation of the cell. Various glycosphingolipids have been identified as associated with human cancer. A particular glycolipid antigen with a type II chain referred to as Lewis$^x$ (Le$^x$) antigen has been related to a number of cancers and is the tumor marker which is identified in the exemplary assay in the Experimental section hereinafter.

Many monoclonal antibodies directed at human tumor associated antigens have been developed and are suitable for use in the assay of the present invention. Illustrative antibodies include R24 specific for a human melanoma antigen (Dippold et al. (1980) Proc. Natl. Acad. Sci. USA 77:6114); monoclonal antibody N-19-9 directed at sialylated Lewis$^a$ antigen (Koprowski et al. (1979) Somatic Cell Genet. 5:957); as well as various antibodies directed at the Le$^x$ structure.

In performing the assay of the present invention, a plasma or serum sample of from about 1 to 10 mls is obtained from the patient and applied to the immunoadsorbent column. The column is then washed, and the bound immune complexes eluted with a suitable chaotropic agent, such as sodium thiocyanate or by changing the pH or ionic conditions. The eluate is returned to physiological pH or conditions, and adjusted to a desired concentration prior to performing the solid-phase assay. The prepared eluates are dispensed into the assay test receptacle and incubated under conditions which allow specific binding of the immune complexes. After washing the test receptacle to remove non-bound substances, the labelling system is introduced and the amount of bound label determined.

The following examples are offered by way of illustration, not by way of limitation.

EXPERIMENTAL

Materials and Methods

The column used for extracorporeal immunoadsorption was obtained from IMRÉ Corporation, Seattle, Wash., and designated by the trade name Prosorba. The Prosorba ™ column comprises protein A isolated from cultures of *Staphylococcus aureus* Cowan I bound to a silica matrix in a cartridge. Prior to use, the column was washed with normal saline followed by a wash with normal saline and heparin.

Extracorporeal immunoadsorption was performed as follows. A catheter was placed into the pulmonary artery to monitor hemodynamic changes. A continuous-flow plasma-cell separator (IBM 2997, Armonk, NY) was used to separate anticoagulated blood into cellular components and plasma. The cellular components were returned unprocessed. The plasma (0.25 to 2L) was perfused over a Prosorba ™ column containing 200 mg protein A and returned to the patient. Eluates were obtained by eluting the Prosorba ™ column with phosphate buffered saline (PBS), pH 11.5, and immediately neutralizing the eluate. Normal human plasma passed over Prosorba ™ columns as control.

Monoclonal antibodies IR-13 and IR-14, available from IMRÉ Corporation, are specific for fucolipids having the X determinant (Gal$\beta$1→4[Fuc$\alpha$1→3]GlcNAc).

The Raji cell assays were performed in small (5 ml) conical test receptacles. The viability of the Raji cells were determined by trypan blue exclusion prior to the assay. Approximately $10^6$ viable cells were used per receptacle. The Raji cells were spun down to remove the culture fluid and resuspended in 1 ml cold PBS. Cells were spun again, and the supernatant was discarded. Column eluates containing 1 mg protein were incubated with the Raji cells for 1 hr at 4° C. After 1 hr the cells were spun and washed 3 times with cold PBS. Cell pellets were suspended in 30% fetal calf serum (FCS) for 1 hr at 4° C. to inhibit non-specific binding of monoclonal antibodies. $Le^x$-specific monoclonal antibody IR-13 in 30% fetal calf serum (FCS) was added to the cells and incubated for 1 hr at 4° C. The PBS-washed Raji cells were then suspended with a peroxidase conjugated rabbit anti-mouse IgG for 1 hr at 4° C. The cells were thoroughly washed, and the enzyme substrate o-phenylenediamine (1 mg/ml containing 25 $\mu$l/30 $\mu$l of 30% $H_2O_2$ as a catalyst) was added for 15 min at room temperature (the cells were spun down and the supernatant was transferred to a microtiter plate). The enzyme reaction was stopped by 1N $H_2SO_4$. The absorbence was measured on an ELISA plate reader at 490 nm.

RESULTS

Extracorporeal immunoadsorption was performed on a patient diagnosed as having breast adenocarcinoma. A Raji cell assay employing the IR-13 antibody and the peroxidase conjugated rabbit anti-mouse antibody was positive for the breast cancer eluate while it was negative for a normal human eluate. The assay was also negative with purified $Le^x$ alone (not in immune complex) or $Le^x$ emulsified with normal human serum.

In order to determine the disease specificity of the $Le^x$-related immune complexes, the assay of the present invention was performed on column eluates containing 1 mg protein from patients suffering from different cancers. The assay was positive in 6/7 breast cancer patients, 4/4 colon cancer patients, and 1/1 lung cancer patients, while it was negative for 3/3 melanoma, 1/1 hepatoma, and 2/2 normal patients. However, when the Raji cell assay was carried out directly on the sera (100 $\mu$l containing approximately 1 mg IgG) of the same patients, none of the sera were positive for the $Le^x$-related complexes. This indicates that enrichment of the complexes relative to other serum components is necessary before the immune complexes associated with specific tumor markers may be detected in serum.

Although the foregoing invention has been described in some detail by way of illustration and example for purposes of clarity of understanding, it will be obvious that certain changes and modifications may be practiced within the scope of the appended claims.

What is claimed is:

1. A method for detecting immune complexes containing a specific antigenic marker in a plasma or serum sample, said method comprising:
    enriching immune complexes relative to other proteins in the sample by a factor of at least 1.2 by passage of the sample through an immunoadsorbent column capable of specifically binding the immune complexes, followed by elution of the enriched sample from the column;
    separating intact immune complexes from the enriched sample by binding to Raji cells or Clq; and
    detecting the specific antigenic marker in the intact complexes separated from the enriched sample.

2. A method as in claim 1, wherein the immunoadsorbent column is a protein A column.

3. A method as in claim 1, wherein the Raji cells or Clq are bound to a solid phase to allow separation of the bound immune complexes from the enriched sample.

4. A method as in claim 1, wherein immune complexes bound to Raji cells are separated from the enriched sample by centrifugation.

5. A method as in claim 1, wherein the specific marker is detected by reaction with an antibody specific for the marker.

6. A method as in claim 5, wherein the specific marker is $Le^x$.

7. A method for screening plasma or serum samples for specific antigenic markers present in immune complexes, said method comprising:
    passing the sample through an immunoadsorbent column capable of specifically binding immune complexes wherein the immunoadsorbent column is a protein A column;
    washing the column to remove all unbound substances;
    eluting the bound immune complexes from the column to form an eluate;
    exposing the eluate to a solid phase receptor capable of specifically binding the immune complexes wherein the solid phase receptor comprises Raji cells or Clq bound to a solid-phase; and
    exposing the immune complexes bound to the solid phase to a labelling system specific for the antigenic markers.

8. A method as in claim 7, wherein the labelling system comprises a first antibody specific for the antigenic marker and a labelled antibody specific for the first antibody.

9. A method as in claim 8, wherein the labelled antibody is labelled with an enzyme.

10. A method as in claim 7, wherein the labelling system comprises a labelled antibody specific for the antigenic marker.

11. A method as in claim 10, wherein the labelled antibody is labelled with a radioactive substance.

* * * * *